United States Patent
Xu et al.

(10) Patent No.: US 10,041,089 B1
(45) Date of Patent: Aug. 7, 2018

(54) RESISTANCE ALLELES IN SOYBEAN

(71) Applicant: Syngenta Participations AG, Basel (CH)

(72) Inventors: Zhanyou Xu, Slater, IA (US); Becky Welsh Breitinger, Research Triangle Park, NC (US); Ju-Kyung Yu, Slater, IA (US)

(73) Assignee: Syngenta Participations AG, Basel (CH)

( * ) Notice: Subject to any disclaimer, the term of this patent is extended or adjusted under 35 U.S.C. 154(b) by 164 days.

(21) Appl. No.: 14/922,266

(22) Filed: Oct. 26, 2015

Related U.S. Application Data

(60) Provisional application No. 62/068,816, filed on Oct. 27, 2014.

(51) Int. Cl.

| | | |
|---|---|---|
| *C12N 15/82* | (2006.01) | |
| *C12Q 1/68* | (2018.01) | |
| *A01H 5/10* | (2018.01) | |
| *C12Q 1/6895* | (2018.01) | |
| *A01H 1/04* | (2006.01) | |

(52) U.S. Cl.
CPC ........... *C12N 15/8285* (2013.01); *A01H 1/04* (2013.01); *C12Q 1/6895* (2013.01); *C12Q 2600/13* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | |
|---|---|---|
| 7,951,998 B2 | 5/2011 | Baley et al. |
| 8,198,509 B2 | 6/2012 | Narvel et al. |
| 2006/0288444 A1 | 12/2006 | McCarroll et al. |
| 2010/0275286 A1* | 10/2010 | Wu ............................ A01H 1/02 800/260 |
| 2011/0173713 A1 | 7/2011 | Bhatti et al. |
| 2013/0047301 A1 | 2/2013 | Klaiber et al. |

FOREIGN PATENT DOCUMENTS

| | | |
|---|---|---|
| WO | 2009/021153 | 2/2009 |
| WO | 2009/067280 | 5/2009 |
| WO | 2013/025773 | 2/2013 |

OTHER PUBLICATIONS

Soybase Soybean Genetic Map, chromosome 13, available at https://www.soybase.org/, accessed Sep. 30, 2017.*
SNP Report for BARC-010501-00676, SoyBase database, available at https://www.soybase.org/, accessed Sep. 30, 2017.*
Sct-033 report, SoyBase database, available at https://www.soybase.org/, accessed Sep. 30, 2017.*
SNP Report for BARC-013633-01184, SoyBase database, available at https://www.soybase.org/, accessed Sep. 30, 2017.*
Xu et al., 2013, Proc. Natl. Acad. Sci. USA 110: 13469-13474.*
Li et al., "SSR mapping and confirmation of the QTL from PI96354 conditioning soybean resistance to southern root-knot nematode", Theor Appl Genet (2001) 103:1167-1173.
Luzzi et al., "A Gene for Resistance to the Southern Root-Knot Nematode in Soybean", Journal of Heredity,1994; 85:484-486.
Tamulonis et al "DNA marker analysis of loci conferring resistanct to RKN in soybean" Theor Appl Genet. 95: 664-670 (1997).
Tamulonis et al "RFLP mapping of resistance to RKN in soybean" Crop Science 37 1903-1909 (1997).

* cited by examiner

*Primary Examiner* — Matthew R Keogh
*Assistant Examiner* — Bratislav Stankovic
(74) *Attorney, Agent, or Firm* — Kevin Markham

(57) ABSTRACT

The present invention relates to methods and compositions for identifying, selecting and/or producing a soybean plant or germplasm having root knot nematode resistance. A soybean plant, part thereof and/or germplasm, including any progeny and/or seeds derived from a soybean plant or germplasm identified, selected and/or produced by any of the methods of the present invention is also provided.

7 Claims, No Drawings

SEQUENCE LISTING

```
<160> NUMBER OF SEQ ID NOS: 20

<210> SEQ ID NO 1
<211> LENGTH: 573
<212> TYPE: DNA
<213> ORGANISM: Glycine max
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (533)..(533)
<223> OTHER INFORMATION: n is a, c, g, or t

<400> SEQUENCE: 1
cccccccccc agacgagaag agacacgcaa ctcgataagt atcacaaaag attacagaag      60
aaaaggaaca ttctcttctc aactatatcc tatttgttgc tgttgctgag gtggttggta     120
accaggatac cccggataac tgccatacat gttgggatcc tgtccagcag caggagcata     180
cccataattt tcataacctt gtgcagcata cccatagtat ccaccaccag aaccagcacc     240
accattccac tggtttggat ctgcctgagc ctgagaaaca gagcattcaa aattcaaact     300
cattaaaaag aatcagaaac atattgaaat caagtgcaga gatgcaacac tataactacc     360
tgtttgtttg aaggactgcg rccccatgaa agacgaacat tttgaccacc caacagggtc     420
ccattcaaca cccgaagtgc ctcttcngca cagctcctgt tgcatgaaaa atcaagacac     480
agtaagagag ctgcctagac tagtgttatc acacaaggtg aatgttcaat aanggagagg     540
ttacattacc tgtctgcgaa tgtgccccccc aaa                                573

<210> SEQ ID NO 2
<211> LENGTH: 23
<212> TYPE: DNA
<213> ORGANISM: Artificial Sequence
<220> FEATURE:
<223> OTHER INFORMATION: PRIMER

<400> SEQUENCE: 2
gggtggtcaa aatgttcgtc ttt                                             23

<210> SEQ ID NO 3
<211> LENGTH: 26
<212> TYPE: DNA
<213> ORGANISM: Artificial Sequence
<220> FEATURE:
<223> OTHER INFORMATION: PRIMER

<400> SEQUENCE: 3
gcagagatgc aacactataa ctacct                                          26
```

<210> SEQ ID NO 4
<211> LENGTH: 14
<212> TYPE: DNA
<213> ORGANISM: Artificial Sequence
<220> FEATURE:
<223> OTHER INFORMATION: PROBE

<400> SEQUENCE: 4
actgcgaccc catg                                                        14

<210> SEQ ID NO 5
<211> LENGTH: 14
<212> TYPE: DNA
<213> ORGANISM: Artificial Sequence
<220> FEATURE:
<223> OTHER INFORMATION: PROBE

<400> SEQUENCE: 5
actgcggccc catg                                                        14

<210> SEQ ID NO 6
<211> LENGTH: 1238
<212> TYPE: DNA
<213> ORGANISM: Glycine max

<400> SEQUENCE: 6 gaagggggaac caaatcttgt tcatccagca ccctactgcc atgtctgcgt agggaaccaa       60
cccacaccct gaaacaaact ctttaatgcc cactagaact tccagcttaa gcatatgctc      120
cagcacatgc agtgaccgga gcagcttcca gctgtttctt tgcagaactg tattttttg       180 ttataaacct ggacaaatca acaagataaa aaaattcaaa aatcagacta tatatacccg      240
tctattgcca gaaacagtrt ccataaataa tgttttgctg acaaataagt gaataacaca      300
gcaatatatg ttatttacaa tactatcact ctgtatgata acaattaaca aagcagataa      360
cagaaggaag gcaaatcatt aagttgtaat ctcaagcaaa acttgatcgt tatttggtca      420
aataggaaat attatgttct ccacgatttc aagaaccaca aggccaccct tacatttcta      480
ggtaagggga atgagataaa cttagacaag agaatcattt aaaaagtgca cgtgaaaggc      540
aaatagttga tatcaaggtt tttaaattgc agtcacaatt atgaatccat ctagaaaatt      600
gcagacaaat gcagttaagg cagccacaaa tgcaattaca aagaccctaa aaaccttgac      660
attgtggttg caattgcagt catggatatg ttttagatat gagtgttgca acttttcccg      720
tgcacactaa aaaggttatc aatagcggac ggcagaacat gtcacaaggc caaaattcca      780
ccatataaac acgccatttc caatggcact gccataacag gcctcccttc aaaaattgct      840
tatgacagaa aggtcggaca atgccacatt atgatgttat ggcaatatgg tggtgctata      900
atggttattt aaaaacattg gaacactact aacttcatcc ttttgaaaaa aataggagag      960
caatattata agcatagtaa tcaatctcgg atagtggtgt gccacagcta actatgaaaa     1020
tgctatagca ggatgaccgc tatttttaaat attatgatac aaagtaaata atttataact     1080
atgaaaatgc tataggacca ttgccatttc catatatctc atgcaaagaa aaatgtatac     1140
tgaagttcca agcaaagcca aaaaacaagt gcacaaaaaa tatttaccta agaagtccc      1200 tccatagcaa ctcaaacatc aaccaatttg taccgttt                             1238

<210> SEQ ID NO 7
<211> LENGTH: 20
<212> TYPE: DNA

```
<213> ORGANISM: Artificial Sequence
<220> FEATURE:
<223> OTHER INFORMATION: PRIMER

<400> SEQUENCE: 7
acctggacaa atcaacaaga                                                     20

<210> SEQ ID NO 8
<211> LENGTH: 22
<212> TYPE: DNA
<213> ORGANISM: Artificial Sequence
<220> FEATURE:
<223> OTHER INFORMATION: PRIMER

<400> SEQUENCE: 8
gacacatctg aatcaccctg ga                                                  22

<210> SEQ ID NO 9
<211> LENGTH: 19
<212> TYPE: DNA
<213> ORGANISM: Artificial Sequence
<220> FEATURE:
<223> OTHER INFORMATION: PROBE

<400> SEQUENCE: 9
tattgccaga aacagtatc                                                      19

<210> SEQ ID NO 10
<211> LENGTH: 17
<212> TYPE: DNA
<213> ORGANISM: Artificial Sequence
<220> FEATURE:
<223> OTHER INFORMATION: PROBE

<400> SEQUENCE: 10
ccagaaacag tgtccat                                                        17

<210> SEQ ID NO 11
<211> LENGTH: 492
<212> TYPE: DNA
<213> ORGANISM: Glycine max
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 11
```

```
atcaaggtct acaaagcaga cacatgtgac atgtaactat atacaaaata tcacgaataa      60
ctccagcagg acctaatccg acatgattgt tacatacaaa cantacaatc acttaacgaa     120
caacaaaact ntaccagaca tgatccaaaa catccttagg cacccaaaag gaatgtaagc     180
tcnaactcta acnttgaaag gtcagaagga gttataagac tcaccagagt cactagacag     240
tggagagtta cgaggagaac ccccaatacc acctacatsa ctactatcaa aacctatggc     300
ttcaagccaa aaactaatcc agggtgattc agatgtgtca cctttcatga agatattgac     360
ctgcatgtta agagctcncc gcctcctggg tgtgatatgc tcttggttaa ggacattatg     420
gggctcccta tgtcccgtnc gatttntgtt cagttttcct gggcattaag ccctcctcag     480
aataaaaaaa ag                                                         492
```

<210> SEQ ID NO 12
<211> LENGTH: 24
<212> TYPE: DNA
<213> ORGANISM: Artificial Sequence
<220> FEATURE:
<223> OTHER INFORMATION: PRIMER

<400> SEQUENCE: 12

```
acagtggaga gttacgagga gaac                                             24
```

<210> SEQ ID NO 13
<211> LENGTH: 22
<212> TYPE: DNA
<213> ORGANISM: Artificial Sequence
<220> FEATURE:
<223> OTHER INFORMATION: PRIMER

<400> SEQUENCE: 13

```
gacacatctg aatcaccctg ga                                               22
```

<210> SEQ ID NO 14
<211> LENGTH: 18
<212> TYPE: DNA
<213> ORGANISM: Artificial Sequence
<220> FEATURE:
<223> OTHER INFORMATION: PROBE

<400> SEQUENCE: 14

```
aataccacct acatcact                                                    18
```

<210> SEQ ID NO 15
<211> LENGTH: 17
<212> TYPE: DNA
<213> ORGANISM: Artificial Sequence
<220> FEATURE:
<223> OTHER INFORMATION: PROBE

<400> SEQUENCE: 15

```
taccacctac atgacta                                                     17
```

<210> SEQ ID NO 16
<211> LENGTH: 1238
<212> TYPE: DNA
<213> ORGANISM: Glycine max

<400> SEQUENCE: 16

```
gaagggaac caaatcttgt tcatccagca ccctactgcc atgtctgcgt agggaaccaa       60
cccacaccct gaaacaaact ctttaatgcc cactagaact tccagcttaa gcatatgctc     120
```

```
cagcacatgc agtgaccgga gcagcttcca gctgtttctt tgcagaactg tattttttg      180 ttataaacct ggacaaatca acaagataaa aaaattcaaa aatcagacta tatatacccg      240
tctattgcca gaaacagtrt ccataaataa tgttttgctg acaaataagt gaataacaca      300
gcaatatatg ttatttacaa tactatcact ctgtatgata acaattaaca aagcagataa      360
cagaaggaag gcaaatcatt aagttgtaat ctcaagcaaa acttgatcgt tatttggtca      420
aataggaaat attatgttct ccacgatttc aagaaccaca aggccaccct tacatttcta      480
ggtaagggga atgagataaa cttagacaag agaatcattt aaaaagtgca cgtgaaaggc      540
aaatagttga tatcaaggtt tttaaattgc agtcacaatt atgaatccat ctagaaaatt      600
gcagacaaat gcagttaagg cagccacaaa tgcaattaca aagaccctaa aaaccttgac      660
attgtggttg caattgcagt catggatatg ttttagatat gagtgttgca acttttcccg      720
tgcacactaa aaaggttatc aatagcggac ggcagaacat gtcacaaggc caaaattcca      780
ccatataaac acgccatttc caatggcact gccataacag gcctcccttc aaaaattgct      840
tatgacagaa aggtcggaca atgccacatt atgatgttat ggcaatatgg tggtgctata      900
atggttattt aaaaacattg gaacactact aacttcatcc ttttgaaaaa aataggagag      960
caatattata agcatagtaa tcaatctcgg atagtggtgt gccacagcta actatgaaaa     1020
tgctatagca ggatgaccgc tattttaaat attatgatac aaagtaaata atttataact     1080
atgaaaatgc tataggacca ttgccatttc catatatctc atgcaaagaa aaatgtatac     1140
tgaagttcca agcaaagcca aaaaacaagt gcacaaaaaa tatttaccta agaagtccc      1200 tccatagcaa ctcaaacatc aaccaatttg taccgttt                            1238
```

<210> SEQ ID NO 17
<211> LENGTH: 37
<212> TYPE: DNA
<213> ORGANISM: Artificial Sequence
<220> FEATURE:
<223> OTHER INFORMATION: PRIMER

<400> SEQUENCE: 17
ggacaaatca acaagataaa aaaattcaaa aatcaga                              37

<210> SEQ ID NO 18
<211> LENGTH: 28
<212> TYPE: DNA
<213> ORGANISM: Artificial Sequence
<220> FEATURE:
<223> OTHER INFORMATION: PRIMER

<400> SEQUENCE: 18
gctgtgttat tcacttattt gtcagcaa                                        28

<210> SEQ ID NO 19
<211> LENGTH: 17
<212> TYPE: DNA
<213> ORGANISM: Artificial Sequence
<220> FEATURE:
<223> OTHER INFORMATION: PROBE

<400> SEQUENCE: 19
ccagaaacag tgtccat                                                    17

<210> SEQ ID NO 20
<211> LENGTH: 17
<212> TYPE: DNA
<213> ORGANISM: Artificial Sequence

```
<220> FEATURE:
<223> OTHER INFORMATION: PROBE

<400> SEQUENCE: 20
ccagaaacag tatccat                                                    17
```

RESISTANCE ALLELES IN SOYBEAN

RELATED APPLICATION INFORMATION

This Application claims the benefit of U.S. Provisional Application No. 62/068,816, filed 27 Oct. 2014, the contents of which are incorporated herein by reference herein.

STATEMENT REGARDING ELECTRONIC FILING OF A SEQUENCE LISTING

A Sequence Listing in ASCII text format, submitted under 37 C.F.R. § 1.821, entitled 80577-US-REG-ORG-NAT-1_Seq_Listing_ST25.txt, 8.63 kilobytes in size, generated on Oct. 6, 2015 and filed via EFS-Web, is provided in lieu of a paper copy. This Sequence Listing is hereby incorporated by reference into the specification for its disclosures.

FIELD OF THE INVENTION

The present invention relates to compositions and methods for identifying, selecting and/or producing soybean plants having root knot nematode (RKN) resistance.

BACKGROUND

Nematodes are elongated symmetrical roundworms that constitute one of the largest and most successful phyla in the animal kingdom. Many nematode species are free-living and feed on bacteria, whereas others have evolved into pests or parasites of plants and animals, including humans.

Nematode pests of plants are responsible for many billions of dollars in economic losses annually. Nematode plant pests feed on stems, buds, leaves and, in particular, on roots of more than 2,000 vegetables, fruits, and ornamental plants, causing an estimated $100-125 billion crop loss worldwide. Nematodes are present throughout the United States (US), but are mostly a problem in warm, humid areas of the south and west, as well as in sandy soils. The most economically damaging plant nematode pest genera belong to the family Heterderidae of the order Tylenchida, and include the cyst nematodes [genera *Heterodera* and *Globodera*, e.g., soybean cyst nematode (*Heterodera glycines*, SCN) and potato cyst nematodes (*G. pallida* and *G. rostochiensis*)], and the root-knot nematodes (genus *Meloidogyne*).

Root-knot nematodes infest thousands of different plant species including vegetables, fruits, and row crops. Cyst nematodes are known to infest tobacco, cereals, sugar beets, potato, rice, corn, soybeans and many other crops. *Heterodera schachtii* (BCN) principally attacks sugar beets, and *Heterodera avenae* is a pest of cereals. *Heterodera zeae* feeds on corn, and *Globodera rostochiensis* and *G. pallida* feed on potatoes. The soybean cyst nematode (SCN) is present in every soybean-producing state in the US, and causes total soybean yield losses estimated to be nearly $1 billion per year. Once SCN is present in a field, it cannot feasibly be eradicated using known methods. Although soybean is the major economic crop attacked by SCN, SCN attacks at least fifty other hosts, including field crops, vegetables, ornamentals, and weeds.

Signs of nematode damage include stunting and yellowing of leaves, as well as wilting of the plants during hot periods. However, nematodes can cause significant yield loss without obvious above-ground symptoms. For example, an infestation of SCN in a plant can result in dwarfed or stunted roots, decrease the number of nitrogen-fixing nodules on the roots, and/or make the roots more susceptible to attack by other soil-borne plant pests or pathogens.

In contrast to many viral and bacterial pathogens, little is known about the molecular basis of the nematode-plant interaction, limiting the available approaches useful in controlling nematodes. Chemicals useful in controlling nematode plant pests include organophosphates and carbamates, the oldest extant class of nematicides, which target acetylcholinesterase. Imidazole derivatives such as benzimidazole exert their nematicidal effects by binding tubulin. Levamisole acts as an agonist on the nicotinic acetylcholine receptor, and avermectins act as irreversible agonists at glutamate-gated chloride channels. Unfortunately, there are certain debilitating nematode infestations which are difficult, if not impossible, to eradicate with existing control measures.

Nematode resistant germplasm and transgenic plants have also been considered as alternatives or complements to chemical control measures. Different varieties of soybean vary in their sensitivity or resistance to root knot nematode infestation. Therefore, one effective control measure for nematode infestation is planting nematode resistant soybean varieties. Accordingly, varietal selection is an important tool for management of nematode infestation. However, currently, determining whether a soybean cultivar might be nematode resistant typically involves testing the phenotype of each cultivar in the field or greenhouse.

Thus, the present invention overcomes shortcomings in the art by providing markers associated with resistance to root knot nematode, thereby allowing the characterization of soybean cultivars for such resistance by molecular analysis rather than phenotypic analysis.

SUMMARY OF THE INVENTION

Compositions and methods for identifying, selecting and/or producing soybean plants with root knot nematode resistance (RKN) are provided. As described herein, a marker associated with RKN resistance may comprise, consist essentially of or consist of a single allele or a combination of alleles at one or more genetic loci.

Accordingly, in some embodiments of the present invention, a method of identifying and/or selecting a root knot nematode (RKN) resistant soybean plant or part thereof is provided, the method comprising: detecting, in said soybean plant or part thereof, at least one allele of a marker locus that is associated with RKN resistance in a soybean plant, wherein said one or more marker locus is located within a chromosomal interval on chromosome 13 defined by and including base pair (bp) position 30771524 (SY0084A) to base pair (bp) position 29825175 (SY0422A), thereby identifying and/or selecting an RKN resistant soybean plant or part thereof.

In some embodiments of the present invention, a method of identifying and/or selecting a root knot nematode (RKN) resistant soybean plant or part thereof is provided, the method comprising: detecting, in said soybean plant or part thereof, the presence of a marker associated with RKN resistance in a soybean plant, wherein said marker is located within a chromosomal interval on chromosome 13 defined by and including an A allele at SY0084A and a C allele at SY0422A, thereby identifying and/or selecting a RKN resistant soybean plant or part thereof.

In some embodiments, a method of identifying and/or selecting a root knot nematode (RKN) resistant soybean plant or part thereof is provided, comprising: detecting, in said soybean plant or part thereof, at least one allele of a marker locus that is associated with RKN resistance in a soybean plant, wherein said one or more marker locus is located within (a) a chromosomal interval on chromosome 13 defined by and including markers Satt663 (physical position 24451347) and Satt490 (physical position 35557764); and/or (b) a chromosomal interval on chromosome 10 defined by and including Sat_196 (physical pos 179136) and Sat_318 (physical position 3167104), thereby identifying and/or selecting a RKN resistant soybean plant or part thereof.

In some embodiments, a method of identifying and/or selecting a root knot nematode (RKN) resistant soybean plant or part thereof is provided, comprising: detecting, in said soybean plant or part thereof, the presence of a combination of markers associated with RKN resistance in a soybean plant, wherein said combination of markers comprises: (a) an A allele at SY0677A or an A allele at SY0033A; (b) an A allele at SY0084A and a C allele at SY0422A; or (c) any combination of (a) and/or (b) above, thereby identifying and/or selecting a RKN resistant soybean plant or part thereof.

In some embodiments, the present invention provides a method of identifying and/or selecting a root knot nematode (RKN) resistant soybean plant or part thereof, comprising: detecting, in said soybean plant or part thereof, the presence of a marker associated with RKN resistance, wherein said marker comprises: (a) an A allele at SY0677A; (b) an A allele at SY0033A; (c) an A allele at SY0084A; (d) a C allele at SY0422A; or (e) one or more markers located within a chromosomal interval on chromosome 13 defined by and including an A allele at SY0084A and a C allele at SY0422A, and (f) any combination of (a) through (e) above, thereby identifying and/or selecting a RKN resistant soybean plant or part thereof.

In some embodiments, a method of producing a root knot nematode (RKN) resistant soybean plant is provided, the method comprising: detecting, in said soybean plant or part thereof, at least one allele of a marker locus that is associated with RKN resistance in a soybean plant, wherein said one or more marker locus is located within a chromosomal interval on chromosome 13 defined by and including base pair (bp) position 30771524 (SY0084A) to base pair (bp) position 29825175 (SY0422A); or (c) any combination of (a) and/or (b) above, thereby producing a RKN resistant soybean plant or part thereof.

In some embodiments, the invention provides a method of producing a root knot nematode (RKN) resistant soybean plant, comprising: detecting, in a soybean germplasm, the presence of a marker associated with RKN resistance in a soybean plant, wherein said marker is located within a chromosomal interval on chromosome 13 defined by and including an A allele at SY0084A and a C allele at SY0422A; and producing a soybean plant from said soybean germplasm, thereby producing a root knot nematode (RKN) resistant soybean plant.

In some embodiments, a method of producing a root knot nematode (RKN) resistant soybean plant is provided, comprising: detecting, in said soybean plant or part thereof, at least one allele of a marker locus that is associated with RKN resistance in a soybean plant, wherein said one or more marker locus is located within (a) a chromosomal interval on chromosome 13 defined by and including markers Satt663 (physical position 24451347) and Satt490 (physical position 35557764); and/or (b) a chromosomal interval on chromosome 10 defined by and including Sat_196 (physical pos 179136) and Sat_318 (physical position 3167104), thereby producing a RKN resistant soybean plant or part thereof.

In some embodiments, a method of producing a root knot nematode (RKN) resistant soybean plant is provided, the method comprising: detecting, in a soybean germplasm, the presence of a combination of markers associated with RKN resistance in a soybean plant, wherein said combination of markers is selected from the group consisting of: (a) an A allele at SY0677A or an A allele at SY0033A; (b) an A allele at SY0084A and a C allele at SY0422A; and (c) any combination of (a) and/or (b) above, and producing a soybean plant from said soybean germplasm, thereby producing RKN resistant soybean plant.

In some embodiments, the invention provides a method of producing a root knot nematode (RKN) resistant soybean plant, comprising: detecting, in a soybean germplasm, the presence of a marker associated with RKN resistance in a soybean plant, wherein said marker comprises: (a) an A allele at SY0677A; (b) an A allele at SY0033A; (c) an A allele at SY0084A; (d) a C allele at SY0422A; or (e) one or more markers located within a chromosomal interval on chromosome 13 defined by and including an A allele at SY0084A and a C allele at SY0422A, and (f) any combination of (a) through (e) above, thereby identifying and/or selecting a RKN resistant soybean plant or part thereof.

In some embodiments, a method of selecting a root knot nematode (RKN) resistant soybean plant or germplasm is provided, the method comprising: crossing a first soybean plant or germplasm with a second soybean plant or germplasm, wherein said first soybean plant or germplasm comprises within its genome a marker associated with RKN resistance in a soybean plant, wherein said marker is located within a a chromosome interval on chromosome 13 defined by and including base pair (bp) position 30771524 (SY0084A) to base pair (bp) position 29825175 (SY0422A); or (c) any combination of (a) and/or (b) above; and selecting a progeny soybean plant or germplasm that comprises said marker within its genome, thereby selecting a RKN resistant soybean plant or germplasm.

In some embodiments, a method of selecting a root knot nematode (RKN) resistant soybean plant or germplasm is provided, the method comprising: crossing a first soybean plant or germplasm with a second soybean plant or germplasm, wherein said first soybean plant or germplasm comprises within its genome a marker associated with RKN resistance in a soybean plant, wherein said marker is located within a chromosomal interval on chromosome 13 defined by and including an A allele at SY0084A and a C allele at SY0422A; and selecting a progeny soybean plant or germplasm that comprises said marker within its genome, thereby selecting a RKN resistant soybean plant or germplasm.

In some embodiments, a method of selecting a root knot nematode (RKN) resistant soybean plant or germplasm is provided, comprising: crossing a first soybean plant or germplasm with a second soybean plant or germplasm, wherein said first soybean plant or germplasm comprises within its genome a marker associated with RKN resistance in a soybean plant, wherein said marker is located within a chromosomal interval on (a) chromosome 13 defined by and including markers Satt663 (physical position 24451347) and Satt490 (physical position 35557764); and/or (b) on chromosome 10 defined by and including Sat_196 (physical pos 179136) and Sat_318 (physical position 3167104); and selecting a progeny soybean plant or germplasm that comprises said marker within its genome, thereby selecting a RKN resistant soybean plant or germplasm.

In some embodiments one may employ gene editing technologies (e.g. CRISPR, TALEN, etc.) to introduce a RKN sequence and/or allele edit into a plant's genome resulting in a plant resistant to RKN as compared to a control plant not comprising said sequence and/or allele edit.

In some embodiments, the invention provides a method of selecting a root knot nematode (RKN) resistant soybean plant or germplasm, comprising: crossing a first soybean plant or germplasm with a second soybean plant or germplasm, wherein said first soybean plant or germplasm comprises within its genome a combination of genetic markers associated with RKN resistance in a soybean plant, wherein the combination of genetic markers comprises: (a) an A allele at SY0677A or an A allele at SY0033A; (b) an A allele at SY0084A and a C allele at SY0422A; and (c) any combination of (a) and/or (b) above, and selecting a progeny soybean plant or germplasm that comprises said markers within its genome, thereby selecting a RKN resistant soybean plant or germplasm.

In some embodiments, a method of selecting a root knot nematode (RKN) resistant soybean plant or germplasm is provided, the method comprising: crossing a first soybean plant or germplasm with a second soybean plant or germplasm, wherein said first soybean plant or germplasm comprises within its genome a marker associated with RKN resistance in a soybean plant, wherein said marker comprises: (a) an A allele at SY0677A; (b) an A allele at SY0033A; (c) an A allele at SY0084A; (d) a C allele at SY0422A; (e) one or more markers located within a chromosomal interval on chromosome 13 defined by and including an A allele at SY0084A and a C allele at SY0422A, (f) any combination of (a) through (e) above; and selecting a progeny soybean plant or germplasm that comprises said marker within its genome, thereby selecting a RKN resistant soybean plant or germplasm.

These and other aspects of the invention are set forth in more detail in the description of the invention below.

DETAILED DESCRIPTION

The present invention provides compositions and methods for identifying, selecting and/or producing soybean plants having root knot nematode resistance, as well as soybean plants, parts thereof, including but not limited to seeds, and soybean germplasm, that are identified, selected and/or produced by methods of this invention. The present invention further provides an assay for the detection of RKN resistance and/or tolerance in a soybean plant, plant part and/or soybean germplasm. In addition, the present invention provides soybean plants, plant parts, and/or germplasm having within their genome one or more SNP or QTL markers associated with resistance to root knot nematode infestation.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with root knot nematode resistance in a soybean plant relative to a control soybean plant not having the target allele or alleles. Thus, for example, a soybean plant comprising one or more of the markers associated with RKN resistance as described herein (e.g., desired alleles) can have RKN resistance or increased RKN resistance as compared to a soybean plant that does not comprise said one or more markers associated with RKN resistance (e.g., desired alleles).

A marker is "associated with" a trait when said trait is linked to the marker and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with a RKN resistance allele" refers to a marker whose presence or absence can be used to predict whether a plant will display root knot nematode resistance.

As used herein, the terms "backcross" and "backcrossing" refer to the process whereby a progeny plant is crossed back to one of its parents one or more times (e.g., 1, 2, 3, 4, 5, 6, 7, 8, 9, 10, or more.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. Marker-assisted Backcrossing: A Practical Example, in TECHNIQUES ET UTILISATIONS DES MARQUEURS MOLECULAIRES LES COLLOQUES, Vol. 72, pp. 45-56 (1995); and Openshaw et al., Marker-assisted Selection in Backcross Breeding, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on. In some embodiments, the number of backcrosses can be about 1 to about 10 (e.g., 1, 2, 3, 4, 5, 6, 7, 8, 9, 10). In some embodiments, the number of backcrosses is about 7.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make up for all the genes in its genome. Genotypes can be indirectly characterized, e.g., using markers and/or directly characterized by, e.g., nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.). In some embodiments, germplasm includes but is not limited to tissue culture.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to a cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, 5, 6, 7, 8, 9, 10 or more times) to a line having a desired genetic background, selecting for the desired allele, with the result being that the desired allele becomes fixed in the desired genetic background. For example, a marker associated with RKN resistance may be introgressed from a donor into a recurrent parent that is RKN susceptible. The resulting offspring could then be backcrossed one or more times and selected until the progeny comprises the genetic marker(s) associated with RKN resistance in the recurrent parent background.

As used herein, the term "linkage" refers to the degree with which one marker locus is associated with another marker locus or some other locus (for example, a RKN resistance locus). The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., RKN resistance. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234:177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of soybean genetic markers are known in the art, and are published or available from various sources, such as the SoyBase internet resource (soybase.org). In some embodiments, a genetic marker of this invention is a SNP allele, a SNP allele located in a chromosome interval and/or a haplotype (combination of SNP alleles), each of which is associated with RKN resistance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Tables 1-3).

Accordingly, in some embodiments of this invention, a marker is detected by amplifying a *Glycine* sp. nucleic acid with two oligonucleotide primers by, for example, an amplification reaction such as the polymerase chain reaction (PCR).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the term "probe" refers to a single-stranded oligonucleotide sequence that will form a hydrogen-bonded duplex with a complementary sequence in a target nucleic acid sequence analyte or its cDNA derivative. Thus, a "marker probe" and "probe" refers to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Non-limiting examples of a probe of this invention includes SEQ ID NO:4 (SY0084A; A allele), SEQ ID NO:5 (SY0084A; G allele), SEQ ID NO:9 (SY0677A; A allele), SEQ ID NO:10 (SY0677A; G allele), SEQ ID NO:14 (SY0422A; C allele), SEQ ID NO:15 (SY0422A; G allele), SEQ ID NO:19 (SY0033A; G allele), and/or SEQ ID NO:20 (SY0033A; A allele).

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules.

Some of the markers described herein can also be referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., technology for SNP detection.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

Non-limiting examples of primers of the invention include SEQ ID NO:2 (SY0084A), SEQ ID NO:3 (SY0084A), SEQ ID NO:7 (SY0677A), SEQ ID NO:8 (SY0677A), SEQ ID NO:12 (SY0422A), SEQ ID NO:13 (SY0422A), SEQ ID NO:17 (SY0033A), and/or SEQ ID NO:18 (SY0033A).

The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least abut 50%, 60%, 70%, 75%, 80%, 85%, 90% or 95% sequence identity. In some embodiments, two nucleotide sequences can have at least about 75%, 80%, 85%, 90%, 95%, or 100% sequence identity, and any range or value therein. In representative embodiments, two nucleotide sequences can have at least about 95%, 96%, 97%, 98%, 99% or 100% sequence identity, and any range or value therein.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLAST®X version 2.0 for translated nucleotide sequences and BLAST®N version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST®) programs, which are publicly available from National Center Biotechnology Information (NCBI) at the National Library of Medicine, National Institute of Health, Bethesda, Md. 20894; see BLAST® Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence, BLAST®X can be used to determine sequence identity; and for polynucleotide sequence, BLAST®N can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, and/or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant part or a plant organ (e.g., leaves, stems, roots, etc.), a plant tissue, a seed and/or a plant cell. A plant cell is a cell of a plant, taken from a plant, or derived through culture from a cell taken from a plant.

As used herein, the term "soybean" refers to a plant, and any part thereof, of the genus *Glycine* including, but not limited to *Glycine max*.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny," "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1 s, F2s and the like. An F1 can thus be (and in some embodiments is) a hybrid resulting from a cross between two true breeding parents (the phrase "true-breeding" refers to an individual that is homozygous for one or more traits), while an F2 can be an offspring resulting from self-pollination of the F1 hybrids.

As used herein, the term "reference sequence" refers to a defined nucleotide sequence used as a basis for nucleotide sequence comparison (e.g., Chromosome 10 or Chromosome 13 of *Glycine max* cultivar Williams 82). The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

Genetic loci correlating with particular phenotypes, such as root nematode resistance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with root knot nematode resistance in soybean. Detection of these markers and/or other linked markers can be used to identify, select and/or produce soybean plants having RKN resistance and/or to eliminate soybean plants from breeding programs or from planting that do not have RKN resistance.

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) Genomics 20:176-183.

Table 1 provides the names of four RKN associated markers (SNPs) of this invention, the physical genetic locations of each marker on the respective soybean chromosome or linkage group, and the target allele that is associated with resistance to RKN.

Markers of the present invention are described herein with respect to the positions of marker loci in the 8X public build of the Williams82 (Wm 82.a1) Schmutz et al. *Nature* 463, 178-183 (14 Jan. 2010) soybean genome at the SoyBase internet resource (soybase.org/SequenceIntro.php) or USDA at (bfgl.anri.barc.usda.gov/cgi-bin/soybean/Linkage.pl). See Table 1, below.

TABLE 1

The respective soybean chromosome or linkage group of physical and genetic positions including the sequence identifiers for the DNA fragments comprising the SNPs and two probe sequences with tagged SNP allele for each assay for the four genetic markers.

| Index | Assay name | Public SNP name/ Locus name | Chromosome | Physical position in Williams82 genome | Linkage group | LG position (cM) | SEQ ID NO for DNA fragment comprising SNP | SEQ ID NO for probe 1 Sequence | Probe 1 detected nucleotide | SEQ ID NO for probe 2 Sequence | Probe 2 detected nucleotide |
|---|---|---|---|---|---|---|---|---|---|---|---|
| 1 | SY0677A | BARC-018101-02517- | 10 | 1571105 | O | 10.753 | 6 | 9 | A | 10 | G |
| 2 | SY0033A | BARC-018101-02517 | 10 | 1571105 | O | 10.753 | 16 | 20 | A | 19 | G |
| 3 | SY0084A | BARC-013633-01184 | 13 | 30771524 | F | | 1 | 4 | A | 5 | G |
| 4 | SY0422A | BARC-029683-06315 | 13 | 29825175 | F | | 11 | 14 | C | 15 | G |

Thus, in some embodiments of this invention, the marker alleles associated with root knot nematode resistance are as set forth in Table 1.

In some embodiments of this invention, the marker allele(s) associated with root knot nematode resistance as set forth in Table 1 can be located in a chromosomal interval including, but not limited to (a) a chromosome interval on chromosome 13 defined by and including base pair (bp) position 30771524 (SY0084A) and to base pair (bp) position 29825175 (SY0422A); (b) a chromosomal interval on chromosome 13 defined by and including an A allele at SY0084A and a C allele at SY0422A; (c) a chromosomal interval on chromosome 13 defined by and including an AA allele at SY0084A and a CC allele at SY0422A and/or of (a) to (c) above. As would be understood by one of skill in the art, additional chromosomal intervals can be defined by the SNP markers provided herein in Table 1.

In some embodiments, a marker allele(s) associated with root knot nematode resistance can be located in a chromosomal interval defined by and including (a) a chromosome interval on chromosome 13 defined by and including markers Satt663 (physical position 24451347) and Satt490 (physical position 35557764); and/or (b) a chromosomal interval on chromosome 10 defined by and including Sat_196 (physical pos 179136) and Sat_318 (physical position 3167104).

In some embodiments, a genetic marker of this invention as set forth in Table 1 is associated with root knot nematode resistance, wherein the genetic marker includes but is not limited to: (a) an A allele at SY0677A; (b) an A allele at SY0033A; (c) an A allele at SY0084A; (d) a C allele at SY0422A; (e) an AA allele at SY0677A; (f) an AA allele at SY0033A; (g) an AA allele at SY0084A; (h) a CC allele at SY0422A; and/or (i) any combination of (a) through (h) above.

In some embodiments, a combination of genetic markers of this invention as set forth in Table 1 is associated with root knot nematode resistance, wherein the combination of genetic markers includes but is not limited to: (a) an A allele at SY0677A or an A allele at SY0033A; (b) an A allele at SY0084A and a C allele at SY0422A; (c) an AA allele at SY0677A or an AA allele at SY0033A; (d) an AA allele at SY0084A and a CC allele at SY0422A; or (e) any combination of (a) and/or (d) above.

Accordingly, this invention further provides methods of identifying, selecting, and/or producing a root knot nematode (RKN) resistant soybean plant or part thereof, comprising: detecting, in said soybean plant or part thereof, the presence of a combination of genetic markers associated with RKN resistance in a soybean plant, as described herein. In further embodiments, the marker can comprise, consist essentially of or consist of any marker linked to the aforementioned markers. That is, any genetic marker that is in linkage disequilibrium with any of the aforementioned markers (SNPs, chromosome intervals and/or combinations of markers (haplotypes)) may also be used to identify, select and/or produce a soybean plant having RKN resistance. Linked markers may be determined, for example, by using resources available on the SoyBase website (soybase.org).

The present invention further provides that the detecting of a molecular marker can comprise the use of a nucleic acid probe having a nucleotide base sequence that is substantially complementary to a nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a marker is designed to determine whether a particular allele of an SNP is present or absent in a particular plant.

Additionally, the methods of this invention include detecting an amplified DNA fragment associated with the presence of a particular allele of a SNP. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length based on a similar reaction with the same primers with the DNA from the plant in which the marker was first detected or the nucleic acid sequence that corresponds (e.g., a homology of at least about 80%, 90%, 95%, 96%, 97%, 98%, 99% or more) to the expected sequence based on the sequence of the marker associated with that SNP in the plant in which the marker was first detected.

The detecting of an amplified DNA fragment having the predicted length or the predicted nucleic acid sequence can be performed by any of a number or techniques, including, but not limited to, standard gel-electrophoresis techniques or by using automated DNA sequencers. Such methods of detecting an amplified DNA fragment are not described here in detail as they are well known to those of ordinary skill in the art.

As shown in Table 1, the SNP markers of this invention are associated with RKN resistance. In some embodiments, as described herein, one marker or a combination of markers can be used to detect the presence of a RKN resistant plant. In some embodiments, a marker can be located within a chromosomal interval (QTL) or be present in the genome of the plant as a haplotype as defined herein.

Thus, methods for identifying and/or selecting a soybean plant or germplasm comprising RKN resistance comprise detecting the presence of a genetic marker (e.g., SNP, SNP located in chromosomal interval (QTL) and/or combination of SNPs) associated with RKN resistance in a soybean plant or part thereof. The genetic marker can be detected in any sample taken from the soybean plant or from a soybean germplasm, including, but not limited to, the whole plant or germplasm or any part thereof (e.g., a seed, a leaf, a tissue culture, a cell, etc.).

Accordingly, in some aspects of the present invention, a method of identifying and/or selecting a RKN resistant soybean plant or part thereof is provided, the method comprising: detecting, in said soybean plant or part thereof, the presence of a marker associated with RKN resistance in a soybean plant, wherein said marker is located within a chromosomal interval comprising, consisting essentially of, or consisting of a chromosome interval on chromosome 13 defined by and including base pair (bp) position 30771524 (SY0084A) to base pair (bp) position 29825175 (SY0422A), thereby identifying and/or selecting a RKN resistant soybean plant or part thereof.

In some embodiments, a method of identifying and/or selecting a RKN resistant soybean plant or part thereof is provided, the method comprising: detecting, in said soybean plant or part thereof, the presence of a marker associated with RKN resistance in a soybean plant, wherein said marker is located within a chromosomal interval comprising, consisting essentially of, or consisting of (a) a chromosome interval on chromosome 13 defined by and including markers Satt663 (physical position 24451347) and Satt490 (physical position 35557764) and/or (b) a chromosomal interval on chromosome 10 defined by and including Sat_196 (physical pos 179136) and Sat_318 (physical position 3167104), thereby identifying and/or selecting a RKN resistant soybean plant or part thereof.

In some embodiments of the present invention, a method of identifying and/or selecting a root knot nematode (RKN) resistant soybean plant or part thereof is provided, the method comprising detecting, in said soybean plant or part thereof, at least one allele of a marker locus that is associated with RKN resistance in a soybean plant, wherein said one or more marker locus is located within a chromosomal interval comprising, consisting essentially of, or consisting of a chromosome interval on chromosome 13 defined by and including base pair (bp) position 30771524 (SY0084A) to base pair (bp) position 29825175 (SY0422A), thereby identifying and/or selecting a RKN resistant soybean plant or part thereof. In some embodiments, each bp position described herein can be defined by an allele, which allele can be heterozygous or homozygous. Accordingly, in some embodiments, the allele at bp position 30771524 (SY0084A) can be an A or an AA, and/or the allele at bp position 29825175 (SY0422A) can be a C or a CC, or any combination thereof. In representative embodiments, the allele at bp position 30771524 (SY0084A) is an AA, and the allele at bp position 29825175 (SY0422A) is a CC.

In some embodiments, a method of identifying and/or selecting a root knot nematode (RKN) resistant soybean plant or part thereof is provided, the method comprising: detecting, in said soybean plant or part thereof, the presence of a marker associated with RKN resistance in a soybean plant, wherein said marker is located within a chromosomal interval comprising, consisting essentially of, or consisting of: a chromosomal interval on chromosome 13 defined by and including an A allele at SY0084A and a C allele at SY0422A, thereby identifying and/or selecting a RKN resistant soybean plant or part thereof. In some embodiments, the alleles defining the chromosome intervals can be independently heterozygous or homozygous. In some embodiments, the allele at SY0084A can be an A or an AA, and/or the allele at SY0422A can be a C or a CC, or any combination thereof. In some embodiments, the detecting, in said soybean plant or part thereof, comprises, consists essentially of, consists of detecting the presence of a marker associated with RKN resistance in a soybean plant, wherein said marker is located within a chromosomal interval comprising, consisting essentially of, or consisting of a chromosomal interval on chromosome 13 defined by and including an AA allele at SY0084A and a CC allele at SY0422A.

In some embodiments, a method of identifying and/or selecting a root knot nematode (RKN) resistant soybean plant or part thereof is provided, comprising: detecting, in said soybean plant or part thereof, the presence of a combination of markers associated with RKN resistance in a soybean plant, wherein said combination of markers comprises, consists essentially of, or consists of: (a) an A allele at SY0677A or an A allele at SY0033A; (b) an A allele at SY0084A and a C allele at SY0422A; or (c) any combination of (a) and/or (b) above, thereby identifying and/or selecting a RKN resistant soybean plant or part thereof.

In some embodiments, the present invention provides a method of identifying and/or selecting a root knot nematode (RKN) resistant soybean plant or part thereof, comprising detecting, in said soybean plant or part thereof, the presence of a marker associated with RKN resistance, wherein said marker comprises, consists essentially of, or consists of: (a) an A allele at SY0677A; (b) an A allele at SY0033A; (c) an A allele at SY0084A; (d) a C allele at SY0422A; and (e) one or more markers located within a chromosomal interval on chromosome 13 defined by and including an A allele at SY0084A and a C allele at SY0422A, and (f) any combination of (a) through (e) above, thereby identifying and/or selecting a RKN resistant soybean plant or part thereof.

In some embodiments, the alleles of said markers can be independently heterozygous or homozygous. In some embodiments, the allele at SY0677A can be an A or an AA, the allele at SY0033A can be an A or an AA, the allele at SY0084A can be an A or an AA, and/or the allele at SY0422A can be a C or a CC, or any combination thereof. In a representative embodiment, the detecting, in said soybean plant or part thereof, comprises, consists essentially of, or consists of detecting the presence of: an AA allele at SY0677A or an AA allele at SY0033A, and an AA allele at SY0084A and a CC allele at SY0422A.

As described herein, methods for identifying and/or selecting a soybean plant or germplasm having RKN resistance can comprise detecting the presence of a marker or a combination of markers associated with RKN resistance.

Any combination of the genetic markers of this invention can be used to identify and/or select a soybean plant or germplasm having RKN resistance.

The subject matter disclosed herein also relates to methods for producing RKN resistant soybean plants comprising detecting the presence of a marker allele or a locus associated with RKN resistance in a donor soybean plant according to the methods as described herein and transferring a nucleic acid sequence comprising at least one allele thus detected from the donor plant to an RKN susceptible soybean plant. The transfer of the nucleic acid sequence can be performed by any of the methods described herein.

Thus, the present invention encompasses methods of plant breeding and methods of selecting/identifying plants, in particular soybean plants, particularly cultivated soybean plants as breeder plants for use in breeding programs or cultivated soybean plants having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example, a plant obtained by inbreeding.

The presently disclosed subject matter thus also provides methods for selecting a plant of the genus *Glycine* exhibiting resistance to RKN comprising detecting in the plant the presence of one or more genetic markers associated with RKN resistance as defined herein. In an exemplary embodiment of the presently disclosed methods for selecting such a plant, the method comprises providing a sample of genomic DNA from a soybean plant; and (b) detecting in the sample of genomic DNA at least one genetic marker associated with RKN resistance as described herein. In some embodiments, the detecting can comprise detecting one or more SNPs, a combination of SNPs (haplotype), and/or SNPs located in chromosomal intervals that are associated with RKN resistance.

The providing of a sample of genomic DNA from a soybean plant can be performed by standard DNA isolation methods well known in the art.

As is well known in the art, the detecting of a genetic marker can in some embodiments comprise the use of one or more sets of primer pairs that can be used to produce one or more amplification products that are suitable for identifying, for example, a SNP. In exemplary embodiments of this invention, the nucleotide sequences comprising the genetic markers (SNPs) are provided (SEQ ID NO:1 (SY0084A), SEQ ID NO:6 (SY0677A), SEQ ID NO:11(SY0422A), SEQ ID NO:16 (SY0033A)) along with probes (SEQ ID NO:4 (SY0084A; A allele), SEQ ID NO:5 (SY0084A; G allele), SEQ ID NO:9 (SY0677A; A allele), SEQ ID NO:10 (SY0677A; G allele), SEQ ID NO:14 (SY0422A; C allele), SEQ ID NO:15 (SY0422A; G allele), SEQ ID NO:19 (SY0033A; G allele), and/or SEQ ID NO:20 (SY0033A; A allele)) and primers for the detection of the markers (SEQ ID NOs:2 and 3 (SY0084A); SEQ ID NOs:7 and 8 (SY0677A); SEQ ID NOs:12 and 13 (SY0422A); SEQ ID NOs:17 and 18 (SY0033A)).

In some embodiments of this invention, a method is provided, said method comprising the transfer by introgression of the nucleic acid sequence from a RKN resistant donor soybean plant into a RKN susceptible recipient soybean plant by crossing the plants. This transfer can be accomplished by using traditional breeding techniques. Loci associated with RKN resistance are introgressed in some embodiments into commercial soybean varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode the desired trait. As disclosed herein, such identification and selection is based on selection of one or more SNP alleles of this invention or markers associated therewith. MAB can also be used to develop near-isogenic lines (NIL) harboring one or more RKN resistance alleles of interest, allowing a more detailed study of an effect of such allele(s), and is also an effective method for development of backcross inbred line (BIL) populations. Soybean plants developed according to these embodiments can in some embodiments derive a majority of their traits from the recipient plant and derive RKN resistance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with RKN resistance into an RKN susceptible recipient soybean plant. For example, inbred RKN resistance soybean plant lines can be developed using the techniques of recurrent selection and backcrossing, selfing, and/or dihaploids, or any other technique used to make parental lines. In a method of recurrent selection and backcrossing, RKN resistance can be introgressed into a target recipient plant (the recurrent parent) by crossing the recurrent parent with a first donor plant, which differs from the recurrent parent and is referred to herein as the "non-recurrent parent." The recurrent parent is a plant that is RKN susceptible or has a low level of RKN resistance and, in some embodiments, comprises commercially desirable characteristics, such as, but not limited to disease and/or insect resistance, valuable nutritional characteristics, valuable abiotic stress tolerance (including, but not limited to, drought tolerance, salt tolerance), and the like. In some embodiments, the non-recurrent parent exhibits RKN resistance and comprises a nucleic acid sequence that is associated with RKN resistance. The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as are known in the art. Alternatively, instead of using bioassays, MAB can be performed using one or more of the hereinbefore described molecular markers, hybridization probes, or polynucleotides to identify those progeny that comprise a nucleic acid sequence associated with RKN resistance. Also, MAB can be used to confirm the results obtained from the quantitative bioassays. In some embodiments, the markers defined herein are suitable to select proper offspring plants by genotypic screening.

Following screening, the F1 hybrid plants that exhibit a RKN resistance phenotype or, in some embodiments, the genotype, and thus comprise the requisite nucleic acid sequence associated with RKN resistance, can then be selected and backcrossed to the recurrent parent for one or more generations in order to allow for the soybean plant to become increasingly inbred. This process can be performed for one, two, three, four, five, six, seven, eight, or more generations.

Thus, a marker that demonstrates linkage with a locus affecting a desired phenotypic trait provides a useful tool for selection of the trait in a plant population. This is particularly true where the phenotype may be difficult to assay or occurs at a late stage in plant development. Since DNA marker assays are less laborious and take up less physical space than field phenotyping, much larger populations can be assayed, increasing the chances of finding a recombinant plant with the target segment from the donor line moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the soybean genome containing increasing densities of public soybean markers has facilitated soybean genetic mapping and MAS. See, e.g. soybeanbreederstoolbox.org, which can be found on the SoyBase website (soybase.org).

Of all the molecular marker types, SNPs are the most abundant and have the potential to provide the highest genetic map resolution (Bhattramakki et al., *Plant Molec. Biol.* 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants, in* PLANT GENO-TYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

Accordingly, the markers of the present invention can be used in marker-assisted selection methods to identify and/or select and/or produce progeny having a genetic marker associated with RKN resistance. Thus, in some embodiments, the present invention relates to methods for producing soybean plants having a RKN resistance associated allele, comprising detecting the presence of at least one allele associated with RKN resistance in a donor soybean plant as described herein, crossing the donor soybean plant with a second soybean plant or germplasm, and detecting in the progeny plant(s) the presence of said at least one allele associated with RKN resistance, thereby transferring the at least one allele associated with RKN resistance thus detected from the donor soybean plant to the second soybean plant and thus producing a soybean plant (e.g., progeny plant) having RKN resistance. In some embodiments, the second soybean plant is RKN susceptible. The transfer of the allele associated with RKN resistance can be performed by any of the methods described herein.

Therefore, in some embodiments of the present invention, a method of producing a root knot nematode (RKN) resistant soybean plant is provided, the method comprising: detecting, in a soybean germplasm, the presence of a marker associated with RKN resistance in a soybean plant, wherein said marker is located within a chromosomal interval comprising, consisting essentially of, or consisting of a chromosome interval on chromosome 13 defined by and including base pair (bp) position 30771524 (SY0084A) to base pair (bp) position 29825175 (SY0422A), and producing a plant from said germplasm, thereby producing a RKN resistant soybean plant.

In some embodiments, a method of producing a root knot nematode (RKN) resistant soybean plant is provided, the method comprising: detecting, in said soybean plant or part thereof, the presence of a marker associated with RKN resistance in a soybean plant, wherein said marker is located within a chromosomal interval comprising, consisting essentially of, or consisting of (a) a chromosome interval on chromosome 13 defined by and including markers Satt663 (physical position 24451347) and Satt490 (physical position 35557764) and/or (b) a chromosomal interval on chromosome 10 defined by and including Sat_196 (physical pos 179136) and Sat_318 (physical position 3167104), and producing a plant from said germplasm, thereby producing a RKN resistant soybean plant.

In some embodiments of the present invention, a method of producing a root knot nematode (RKN) resistant soybean plant is provided, the method comprising: detecting, in a soybean germplasm, at least one allele of a marker locus that is associated with RKN resistance in a soybean plant, wherein said one or more marker locus is located within a chromosomal interval comprising, consisting essentially of, or consisting of a chromosome interval on chromosome 13 defined by and including base pair (bp) position 30771524 (SY0084A) to base pair (bp) position 29825175 (SY0422A), and producing a soybean plant from said soybean germplasm, thereby producing a root knot nematode (RKN) resistant soybean plant.

In some embodiments, the base pair positions defining the chromosomal intervals can comprise alleles, which can be independently heterozygous or homozygous. Thus, in some embodiments, the allele at bp position 1571105 (SY0677A) can be an A or an AA, the allele at bp position 1571105 (SY0033A) can be an A or an AA, the allele at bp position 30771524 (SY0084A) can be an A or an AA, and/or the allele at bp position 29825175 (SY0422A) can be a C or a CC, or any combination thereof. In representative embodiments, the allele at bp position 1571105 (SY0677A) is an AA, the allele at bp position 1571105 (SY0033A) is an AA, the allele at bp position 30771524 (SY0084A) is an AA, and the allele at bp position 29825175 (SY0422A) is a CC.

In some embodiments of the present invention, a method of producing a root knot nematode (RKN) resistant soybean plant is provided, the method comprising: detecting, in said soybean plant or part thereof, the presence of a marker associated with RKN resistance in a soybean plant, wherein said marker is located within a chromosomal interval comprising, consisting essentially of, or consisting of a chromosomal interval on chromosome 13 defined by and including an A allele at SY0084A and a C allele at SY0422A, and producing a soybean plant from said soybean germplasm, thereby producing a root knot nematode (RKN) resistant soybean plant.

In some embodiments, the alleles defining the chromosome intervals can be independently heterozygous or homozygous. In some embodiments, the allele at SY0677A can be an A or an AA, the allele at SY0033A can be an A or an AA, the allele at SY0084A can be an A or an AA, and/or the allele at SY0422A can be a C or a CC, or any combination thereof. In some embodiments, the detecting, in said soybean plant or part thereof, comprises, consists essentially of, or consists of detecting the presence of a marker associated with RKN resistance in a soybean plant, wherein said marker is located within a chromosomal interval comprising, consisting essentially of, or consisting of a chromosomal interval on chromosome 13 defined by and including an AA allele at SY0084A and a CC allele at SY0422A.

In some embodiments, a method of producing a root knot nematode (RKN) resistant soybean plant is provided, the method comprising: detecting, in a soybean germplasm, the presence of a combination of markers associated with RKN resistance in a soybean plant, wherein said combination of markers comprises, consists essentially of, or consists of: (a) an A allele at SY0677A or an A allele at SY0033A; (b) an A allele at SY0084A and a C allele at SY0422A; or (c) any combination of (a) and/or (b) above, and producing a soybean plant from said soybean germplasm, thereby producing a RKN resistant soybean plant.

In some embodiments, the invention provides a method of producing a root knot nematode (RKN) resistant soybean plant, comprising: detecting, in a soybean germplasm, the presence of one or more markers associated with RKN resistance in a soybean plant, wherein said marker comprises, consists essentially of, or consists of: (a) an A allele at SY0677A; (b) an A allele at SY0033A; (c) an A allele at SY0084A; (d) a C allele at SY0422A; or (e) one or more markers located within a chromosomal interval on chromosome 13 defined by and including an A allele at SY0084A and a C allele at SY0422A, (0 any combination of (a) through (e) above, and producing a soybean plant from said soybean germplasm, thereby producing a RKN resistant soybean plant.

In some embodiments, the alleles of said markers (e.g., SY SY0677A, SY0033A, SY0084A, SY0422A) can be independently homozygous or heterozygous. Thus, in some embodiments, the allele at SY0677A can be A or AA, the allele at SY0033A can be A or AA, the allele at SY0084A can be A or AA, and/or the allele at SY0422A can be C or CC, or any combination thereof. In some embodiments, the detecting in a soybean germplasm, comprises detecting the presence of: (a) an AA allele at SY0677A or an AA allele at SY0033A; and (b) an AA allele at SY0084A and a CC allele at SY0422A.

In some embodiments, a method of selecting a root knot nematode (RKN) resistant soybean plant and/or germplasm is provided, the method comprising: crossing a first soybean plant or germplasm with a second soybean plant or germplasm, wherein said first soybean plant or germplasm comprises within its genome a marker associated with RKN resistance in a soybean plant, wherein said marker is located within a chromosomal interval comprising, consisting essentially of, or consisting of (a) a chromosome interval on chromosome 13 defined by and including markers Satt663 (physical position 24451347) and Satt490 (physical position 35557764) and/or (b) a chromosomal interval on chromosome 10 defined by and including Sat_196 (physical pos 179136) and Sat_318 (physical position 3167104), and producing a plant from said germplasm, thereby producing a RKN resistant soybean plant and selecting a progeny soybean plant or germplasm that comprises said marker within its genome, thereby selecting a RKN resistant soybean plant and/or germplasm.

In some embodiments, a method of selecting a root knot nematode (RKN) resistant soybean plant and/or germplasm is provided, the method comprising: crossing a first soybean plant or germplasm with a second soybean plant or germplasm, wherein said first soybean plant or germplasm comprises within its genome a marker associated with RKN resistance in a soybean plant, wherein said marker is located within a chromosomal interval comprising, consisting essentially of, or consisting of a chromosome interval on chromosome 13 defined by and including base pair (bp) position 30771524 (SY0084A) to base pair (bp) position 29825175 (SY0422A); and selecting a progeny soybean plant or germplasm that comprises said marker within its genome, thereby selecting a RKN resistant soybean plant and/or germplasm.

In some embodiments, a method of selecting a root knot nematode (RKN) resistant soybean plant and/or germplasm is provided, the method comprising: crossing a first soybean plant or germplasm with a second soybean plant or germplasm, wherein said first soybean plant or germplasm comprises within its genome one or more marker loci associated with RKN resistance in a soybean plant, wherein said marker loci are located within a chromosomal interval comprising, consisting essentially of, or consisting of: a chromosome interval on chromosome 13 defined by and including base pair (bp) position 30771524 (SY0084A) to base pair (bp) position 29825175 (SY0422A); and selecting a progeny soybean plant or germplasm that comprises said one or more marker loci within its genome, thereby selecting RKN resistant soybean plant and/or germplasm.

In some embodiments, the base pair positions defining the chromosomal intervals can comprise alleles, which can be independently heterozygous or homozygous. Thus, in some embodiments, the allele at bp position 30771524 (SY0084A) can be an A or an AA, and/or the allele at bp position 29825175 (SY0422A) can be a C or a CC. In representative embodiments, the allele at bp position 30771524 (SY0084A) is an AA, and the allele at bp position 29825175 (SY0422A) is a CC.

In some embodiments, a method of selecting a root knot nematode (RKN) resistant soybean plant and/or germplasm is provided, the method comprising: crossing a first soybean plant or germplasm with a second soybean plant or germplasm, wherein said first soybean plant or germplasm comprises within its genome a marker associated with RKN resistance in a soybean plant, wherein said marker is located within a chromosomal interval comprising, consisting essentially of, or consisting of a chromosomal interval on chromosome 13 defined by and including an A allele at SY0084A and a C allele at SY0422A; and selecting a progeny soybean plant or germplasm that comprises said marker within its genome, thereby selecting a RKN resistant soybean plant and/or germplasm. In some embodiments, the alleles can be independently heterozygous or homozygous. Thus, in some embodiments, the allele at SY0084A can be an A or an AA, and/or the allele at SY0422A can be a C or a CC, or any combination thereof. In representative embodiments, the allele at SY0084A is an AA and the allele at SY0422A is a CC.

In some embodiments, the invention provides a method of selecting a root knot nematode (RKN) resistant soybean plant and/or germplasm, comprising: crossing a first soybean plant or germplasm with a second soybean plant or germplasm, wherein said first soybean plant or germplasm comprises within its genome a combination of genetic markers associated with RKN resistance in a soybean plant, the combination of genetic markers comprising, consisting essentially of, or consisting of: (a) an A allele at SY0677A and an A allele at SY0033A; (b) an A allele at SY0084A and a C allele at SY0422A; or (c) any combination of (a) and/or (b) above, and selecting a progeny soybean plant or germplasm that comprises said marker within its genome, thereby selecting a RKN resistant soybean plant and/or germplasm.

In some embodiments, a method of selecting a root knot nematode (RKN) resistant soybean plant and/or germplasm is provided, the method comprising: crossing a first soybean plant or germplasm with a second soybean plant or germplasm, wherein said first soybean plant or germplasm comprises within its genome a marker associated with RKN resistance in a soybean plant, wherein said marker is selected from the group consisting of: (a) an A allele at SY0677A; (b) an A allele at SY0033A; (c) an A allele at SY0084A; (d) a C allele at SY0422A; and (e) one or more markers located within a chromosomal interval on chromosome 13 defined by and including an A allele at SY0084A and a C allele at SY0422A, (f) any combination of (a) through (e) above; and selecting a progeny soybean plant or germplasm that comprises said marker within its genome, thereby selecting a RKN resistant soybean plant and/or germplasm.

In some embodiments, said allele at SY0677A, at SY0033A, at SY0084A and/or at SY0422A can be independently heterozygous or homozygous. Thus, in some embodiments, the allele at SY0677A can be an A or an AA, the allele at SY0033A can be an A or an AA, the allele at SY0084A can be an A or an AA, and/or the allele at SY0422A can be a C or a CC, or any combination thereof. In representative embodiments, the combination of genetic markers can comprise an AA at SY0677A or an AA at SY0033A, and an AA at SY0084A and a CC at SY0422A.

In some embodiments, the second soybean plant or germplasm of this invention is of an elite variety of soybean. In some embodiments, the genome of the second soybean plant or germplasm is at least about 50%, 55%, 60%, 65%, 70%, 75%, 80%, 85%, 90%, 95%, 97%, 99% or 100% identical to that of an elite variety of soybean.

In some embodiments of this invention, a method of introgressing a genetic marker associated with root knot nematode (RKN) resistance into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with RKN resistance in a soybean plant, wherein said marker is located within (a) a chromosome interval on chromosome 13 defined by and including markers Satt663 (physical position 24451347) and Satt490 (physical position 35557764) and/or (b) a chromosomal interval on chromosome 10 defined by and including Sat_196 (physical pos 179136) and Sat_318 (physical position 3167104), and producing a RKN resistant soybean plant or germplasm comprising said genetic marker associated with RKN resistance in the genetic background of the recurrent parent, thereby introgressing the genetic marker associated with RKN resistance into a genetic background lacking said marker. In some embodiments, the base pair positions defining the chromosomal intervals can comprise alleles, which can be heterozygous or homozygous, or any combination thereof.

In some embodiments of this invention, a method of introgressing a genetic marker associated with root knot nematode (RKN) resistance into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with RKN resistance in a soybean plant, wherein said marker is located within a chromosome interval on chromosome 13 defined by and including base pair (bp) position 30771524 (SY0084A) to base pair (bp) position 29825175 (SY0422A), and producing a RKN resistant soybean plant or germplasm comprising said genetic marker associated with RKN resistance in the genetic background of the recurrent parent, thereby introgressing the genetic marker associated with RKN resistance into a genetic background lacking said marker. In some embodiments, the base pair positions defining the chromosomal intervals can comprise alleles, which can be heterozygous or homozygous, or any combination thereof.

In some embodiments, a method of introgressing one or more marker loci associated with RKN resistance in a soybean plant is provided, the method comprising: crossing a donor comprising said one or more marker loci with a recurrent parent that lacks said one or more marker loci; and backcrossing progeny comprising said one or more marker loci with the recurrent parent, wherein said progeny are identified by detecting in their genome the presence of one or more marker loci associated with RKN resistance in a soybean plant, wherein said one or more marker loci are located within a chromosome interval defined by and including base pair (bp) position 30771524 (SY0084A) to base pair (bp) position 29825175 (SY0422A); and selecting a progeny soybean plant or germplasm that comprises said one or more marker loci within its genome, thereby selecting RKN resistant soybean plant or germplasm. In some embodiments, the base pair positions defining the chromosomal intervals can comprise alleles, which can be independently heterozygous or homozygous.

In some embodiments of this invention, a method of introgressing a genetic marker associated with root knot nematode (RKN) resistance in a soybean plant into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with RKN resistance in a soybean plant, wherein said marker is located within a chromosomal interval comprising, consisting essentially of, or consisting of a chromosomal interval on chromosome 13 defined by and including an A allele at SY0084A and a C allele at SY0422A, thereby producing a RKN resistant soybean plant or germplasm comprising said genetic marker associated with RKN resistance in the genetic background of the recurrent parent, thereby introgressing the genetic marker associated with RKN resistance into a genetic background lacking said marker.

In some embodiments, the present invention provides a method of introgressing a genetic marker associated with root knot nematode (RKN) resistance in a soybean plant into a genetic background lacking said marker, the method comprising: crossing a donor soybean plant comprising said marker with a recurrent parent soybean plant that lacks said marker; and backcrossing progeny soybean plants comprising said marker with the recurrent parent soybean plant, wherein said progeny soybean plants are identified by detecting in their genome the presence of a combination of markers associated with RKN resistance in a soybean plant, wherein said combination of markers comprises, consists essentially of, or consists of: (a) an A allele at SY0677A or an A allele at SY0033A; (b) an A allele at SY0084A and a C allele at SY0422A; or (c) any combination of (a) and/or (b) above, thereby producing a RKN resistant soybean plant or germplasm comprising said genetic marker associated with RKN resistance in the genetic background of the recurrent parent soybean plant, thereby introgressing the genetic marker associated with RKN resistance into a genetic background lacking said marker.

In some embodiments of this invention, a method of introgressing a genetic marker associated with root knot nematode (RKN) resistance in a soybean plant into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with RKN resistance in a soybean plant, wherein said marker comprises, consists essentially of, or consists of: (a) an A allele at SY0677A; (b) an A allele at SY0033A; (c) an A allele at SY0084A; (d) a C allele at SY0422A; or (e) one or more markers located within a chromosomal interval on chromosome 13 defined by and including an A allele at SY0084A and a C allele at SY0422A, or (f) any combination of (a) through (e) above, thereby producing a RKN resistant soybean plant or germplasm comprising said genetic marker associated with RKN resistance in the genetic background of the recurrent parent, thereby introgressing the genetic marker associated with RKN resistance into a genetic background lacking said marker.

In embodiments of the invention described above, the alleles at base pair positions defining the chromosomal intervals comprising markers associated with RKN resistance and the alleles of the markers associated with RKN resistance can be independently heterozygous or homozygous. Thus, in some embodiments, the methods of introgressing comprise, consist essentially of, or consist of an A or an AA at base pair position 1571105 or SY0677A; an A or an AA at base pair position 1571105 or SY0033A; an A or an AA base pair position 30771524 or SY0084A; and/or a C or a CC at base pair position 29825175 or SY0422A. In representative embodiments, the allele at bp position 1571105 or SY0677A is an AA, the allele at bp position 1571105 or SY0033A is an AA, the allele at bp position 30771524 or SY0084A is an AA, and the allele at bp position 29825175 or SY0422A is a CC.

The present invention provides soybean plants and germplasms having RKN resistance. As discussed above, the methods of the present invention can be utilized to identify, produce and/or select a soybean plant or germplasm having RKN resistance. In addition to the methods described above, a soybean plant or germplasm having RKN resistance may be produced by any method whereby a marker associated with RKN resistance in a soybean plant is introduced into the soybean plant or germplasm by such methods that include, but are not limited to, transformation (including, but not limited to, bacterial-mediated nucleic acid delivery (e.g., via *Agrobacteria*)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof, protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a soybean plant, or part thereof, having a genetic marker associated with RKN resistance, obtainable by the methods of the presently disclosed subject matter, are aspects of the presently disclosed subject matter. The soybean plant, or part thereof, or soybean germplasm of this invention having a genetic marker associated with RKN resistance can be heterozygous or homozygous for the genetic marker.

In some embodiments, the soybean plant or germplasm may be the progeny of a cross between an elite variety of soybean and a variety of soybean that comprises an allele associated with RKN resistance. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The soybean plant or germplasm may be the progeny of an introgression wherein the recurrent parent is an elite variety of soybean and the donor comprises a genetic marker associated (e.g., SNP, combination of SNPs, SNP located in a chromosome interval) with RKN resistance in a soybean plant as described herein.

The soybean plant or germplasm may be the progeny of a cross between a first elite variety of soybean (e.g., a tester line) and the progeny of a cross between a second elite variety of soybean (e.g., a recurrent parent) and a variety of soybean that comprises a genetic marker associated with RKN resistance in a soybean plant as described herein (e.g., a donor).

The soybean plant or germplasm may be the progeny of a cross between a first elite variety of soybean and the progeny of an introgression wherein the recurrent parent is a second elite variety of soybean and the donor comprises a genetic marker associated with RKN resistance in a soybean plant.

Another aspect of the presently disclosed subject matter relates to a method of producing seeds that can be grown into RKN resistant soybean plants. In some embodiments, the method comprises providing an RKN resistant soybean plant of this invention, crossing the RKN resistant soybean plant with another soybean plant, and collecting seeds resulting from the cross, which when planted, produce RKN resistant soybean plants.

Accordingly, the present invention provides improved soybean plants, seeds, and/or soybean tissue culture produced by the methods described herein.

In some embodiments, the presently disclosed subject matter provides methods for analyzing the genomes of soybean plants/germplasms to identify those that include desired markers associated with RKN resistance. In some embodiments, the methods of analysis comprise amplifying subsequences of the genomes of the soybean plants/germplasms and determining the nucleotides present in one, some, or all positions of the amplified subsequences.

Thus, in some embodiments, the present invention provides compositions comprising one or more amplification primer pairs that initiate DNA polymerization by a DNA polymerase on a *Glycine max* nucleic acid template to generate a *Glycine max* amplicon. In some embodiments, the *Glycine max* marker amplicon corresponds to a *Glycine max* marker comprising a nucleotide sequence of any of SEQ ID NOs:1, 6, 11 and 16. In view of the disclosure of SEQ ID NOs:1, 6, 11 and 16 as being linked to RKN resistance loci, one of ordinary skill in the art would be aware of various techniques that could be employed to analyze the sequences of the corresponding soybean nucleic acids.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

That which is claimed:

1. A method of producing a root knot nematode (RKN) resistant soybean plant, said method comprising the steps of:
   (a) isolating nucleic acids from a soybean plant selected from population of soybean plants;
   (b) detecting in the nucleic acids of (a) at least one allele of a marker locus that is associated with RKN resistance in a soybean plant, wherein said marker locus is located within a chromosomal interval on *Glycine max* chromosome 13 defined by and including base pair (bp) position 30771524 (SY0084A) and to base pair (bp) position 29825175 (SY0422A), wherein the chromosomal interval comprises an allele corresponding to an A at physical position 30771524 and a C at physical position 29825175;
   (c) selecting a first soybean plant from the population of (a) based on the presence of the marker locus of (b);
   (d) crossing the first soybean plant of (c) with a second soybean plant not comprising in its genome the marker detected in (b);
   (e) collecting seed from the cross of (d); and
   (f) growing a progeny soybean plant from the seed of (e), wherein said progeny soybean plant comprises in its genome said marker locus associated with RKN resistance, thereby producing a RKN resistant soybean plant.

2. The method of claim 1, wherein the allele of (b) is homozygous.

3. The method of claim 1, wherein the allele is detected through the use of a nucleotide probe comprising a nucleotide sequence as depicted in any one of SEQ ID NOs: 4, 5, 14 or 15.

4. The method of claim 1, wherein the allele is detected through use of a PCR primer pair that anneals to said chromosomal interval, wherein the primer pair is capable of initiating DNA polymerization by a DNA polymerase on a *Glycine max* nucleic acid template to generate an amplicon determinative for the presence of said marker locus associated with RKN resistance.

5. The method of claim 4, wherein the resulting amplicon comprises a nucleotide sequence comprising either SEQ ID NO: 1 or SEQ ID NO: 11.

6. The method of claim 4, wherein the PCR primer pair comprises SEQ ID NOs: 2 and 3.

7. The method of claim 4, wherein the PCR primer pair comprises SEQ ID NOs: 12 and 13.

\* \* \* \* \*